United States Patent [19]

Brocklehurst

[11] 3,981,763
[45] Sept. 21, 1976

[54] APPARATUS FOR THE MANUFACTURE OF DISPOSABLE DIAPERS OR OTHER ARTICLES HAVING STOP MOTION DEVICES THEREIN

[75] Inventor: Charles E. Brocklehurst, Honea Path, S.C.

[73] Assignee: Riegel Textile Corporation, New York, N.Y.

[22] Filed: Feb. 11, 1975

[21] Appl. No.: 549,049

Related U.S. Application Data

[62] Division of Ser. No. 385,832, Aug. 6, 1973, abandoned.

[52] U.S. Cl. ............................... 156/352; 156/519
[51] Int. Cl.² ........................................ B65C 9/40
[58] Field of Search ........................ 156/350–352, 156/364–368, 519–521; 192/125 A; 198/127, 37; 271/258

[56] References Cited
UNITED STATES PATENTS

| | | | |
|---|---|---|---|
| 2,865,262 | 12/1958 | Fradenburgh | 192/125 A |
| 3,109,527 | 11/1963 | Sisson | 192/125 A |
| 3,745,081 | 7/1973 | Erekson | 156/521 X |
| 3,751,321 | 8/1973 | Hagemann et al. | 156/368 X |
| 3,861,983 | 1/1975 | Harrell | 156/367 X |

Primary Examiner—David A. Simmons
Attorney, Agent, or Firm—Bell, Seltzer, Park & Gibson

[57] ABSTRACT

Apparatus for the manufacture of disposable diapers having spaced apart fastener tabs, labels or strips at predetermined locations thereon including a device for continuously moving material being manufactured into such articles through said apparatus and for applying such fastener tabs, labels or strips at predetermined locations to the moving material and having the following devices in combination therewith. Electrically operated drive devices are provided for driving the tab applying devices and the material moving devices. Sensing devices sense the passage of applied tabs on the moving material. An electric circuit is connected with the sensing devices and with the drive devices for normally operating the drive devices and is responsive to the sensing devices for stopping operating of the drive devices when the sensing devices fail to sense the passage of a tab at a predetermined location on the moving material as it passes the sensing devices.

7 Claims, 12 Drawing Figures

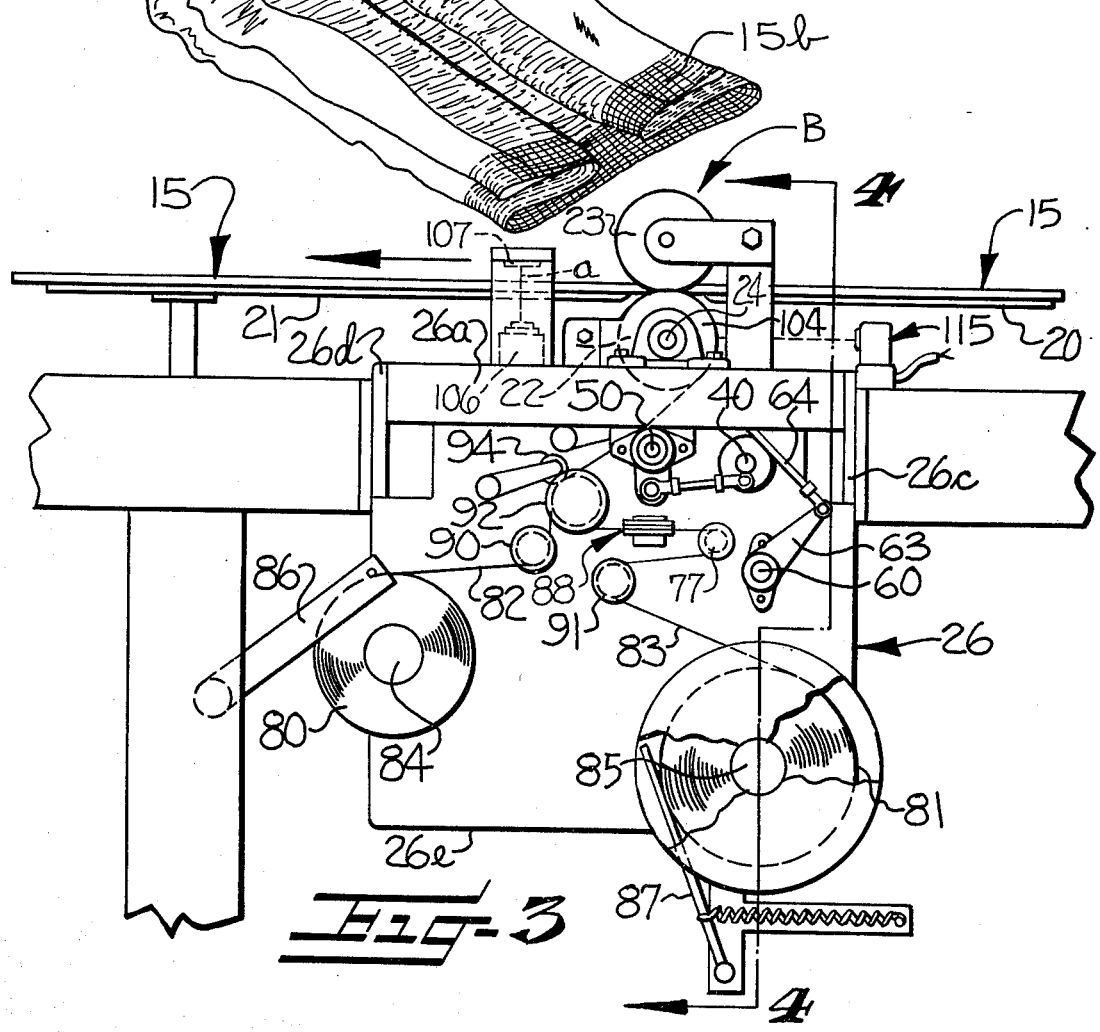

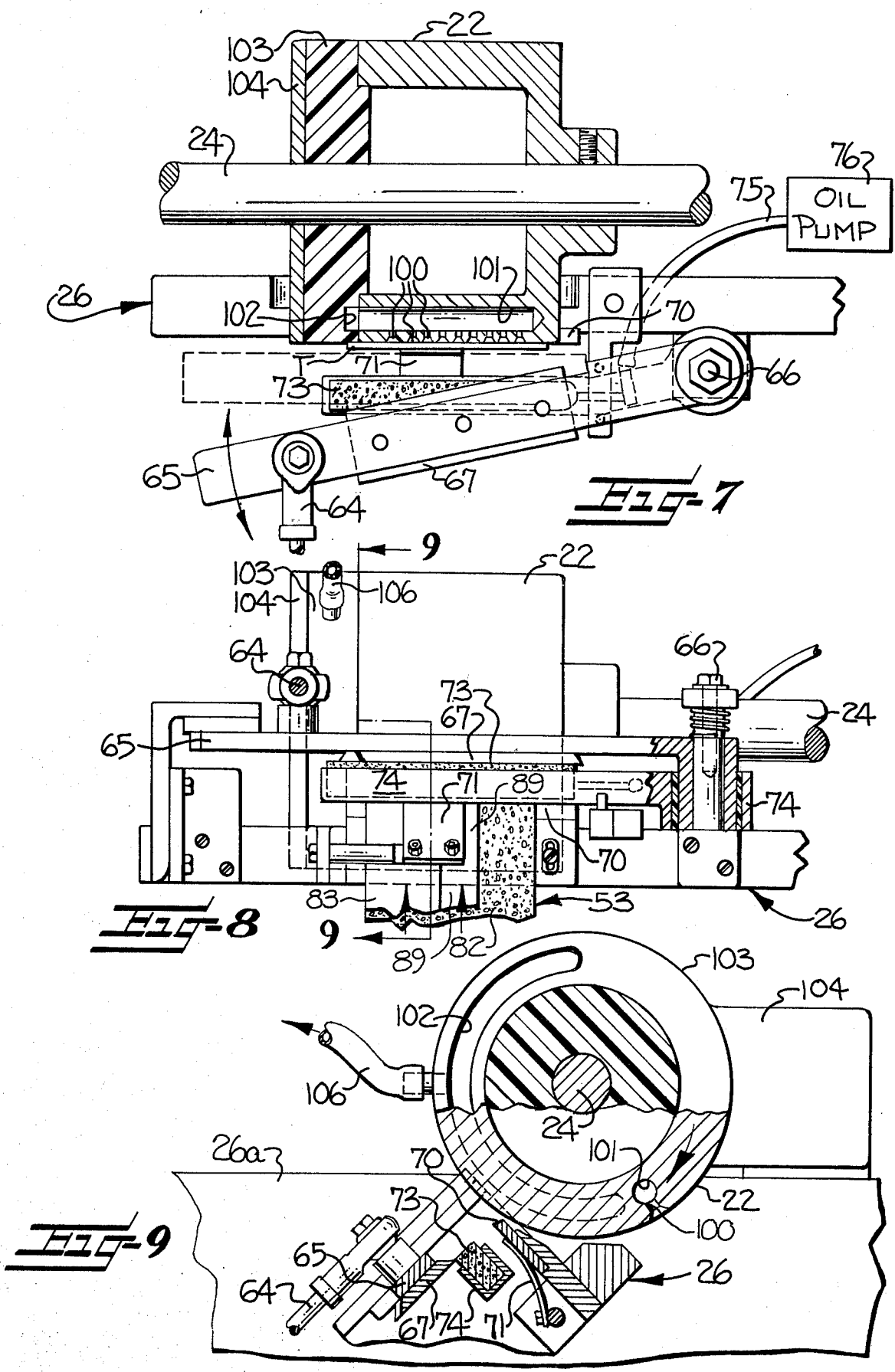

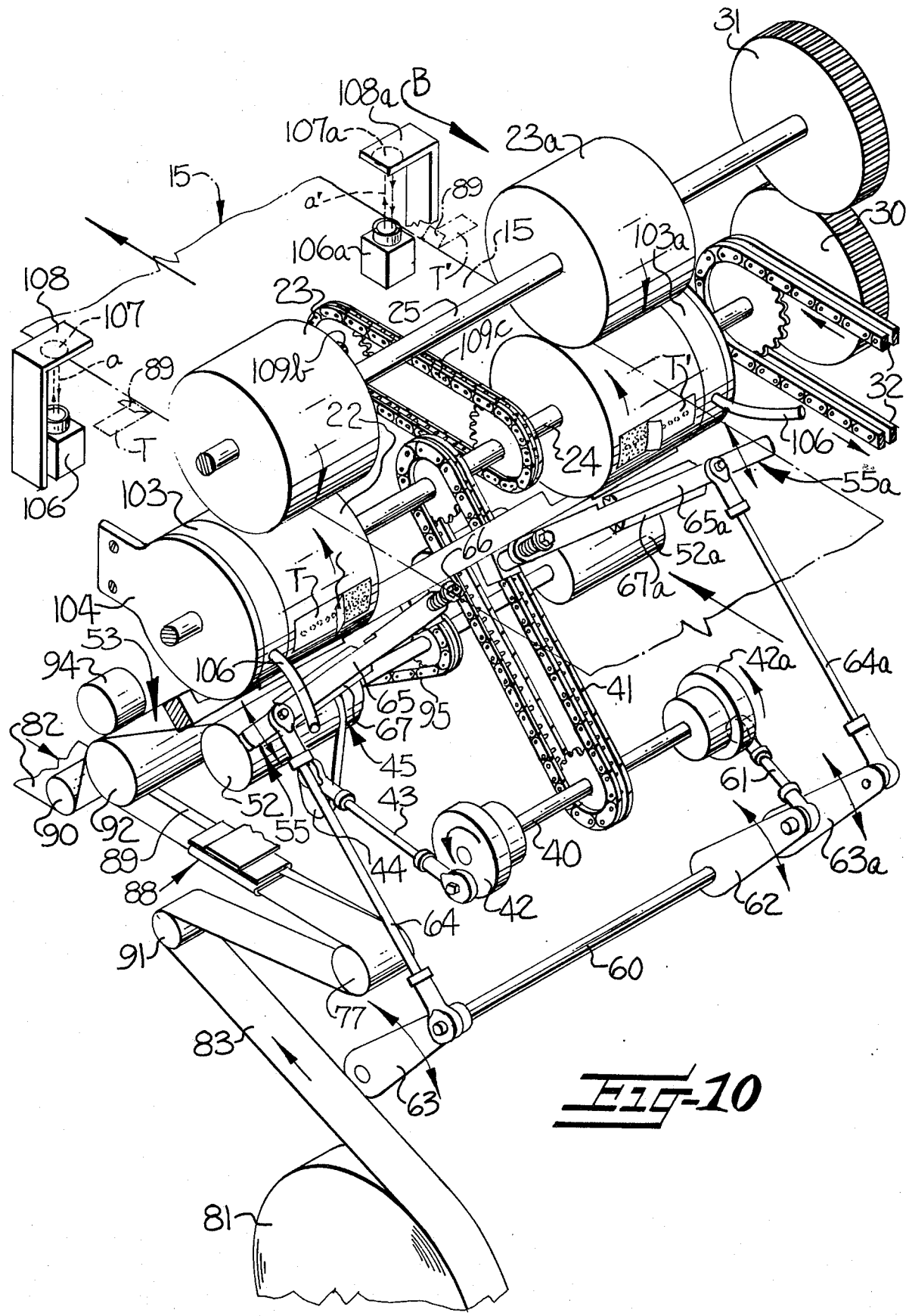

APPARATUS FOR THE MANUFACTURE OF DISPOSABLE DIAPERS OR OTHER ARTICLES HAVING STOP MOTION DEVICES THEREIN

This application is a division of copending application Ser. No. 385,832, filed Aug. 6, 1973 and entitled METHOD AND APPARATUS FOR APPLYING ADHESIVE FASTENER TABS TO A WEB OR DIAPER FORMING MATERIAL, and now abandoned.

This invention generally relates to forming and applying labels, adhesive fastener tabs or strips and the like to moving webs and is particularly concerned with the forming and applying of pressure sensitive fastener tabs to opposite longitudinal edges of a web of diaper-forming material as each successive predetermined length thereof passes through a fastener tab forming and applying station in its course from a web assembling station to a diaper folding station such as are disclosed in U.S. Pat. No. 3,661,680, dated May 9, 1972, reissued as U.S. Pat. No. Re. 38,139 on Aug. 27, 1974, and assigned to the assignee of the present invention.

As is well known, diapers are conventionally secured about a baby's body by safety pins, the use of which is time consuming and oftentimes hazardous. Thus, it is highly desirable, particularly with disposable diapers, to provide adhesive strips or tabs, preferably of the pressure sensitive type, on opposite sides of the diaper so as to provide a readily available and convenient means for securing the diaper about the baby's body. Usually, two adhesive fastener tabs secured to opposite longitudinal side edges of a diaper, adjacent one of its ends, serve quite well for effectively securing the diaper about the baby's body.

Heretofore, it has been the general practice to secure such fastener tabs to a disposable diaper after it has been manufactured or in an operation completely separate from the equipment for effecting the sheet and pad assembling operations and the folding operations attendant to production-line manufacture of disposable diapers. This practice and the apparatus utilized therefor has not been commercially satisfactory.

Apparatus has also been proposed for applying adhesive closure strips to package forming webs, for example, in which a tape-applying roll was positioned adjacent the moving web with a peripheral portion of the roll overlapping the edge of the web and rotatable against the overlapping portion of the web, with means for continuously feeding a strip of adhesive tape to the roll and means cooperating with the roll for cutting the strips of adhesive tape into short lengths to form the closure tapes therefrom as each successive closure tape was temporarily held against the periphery of the tape-applying roll and transferred to the overlapping part of the moving web of packaging material.

Such known apparatus has had the drawback that, during the transfer of each cut length of the strip of closure tape to the overlapping portion of the moving web, it was necessary that the tape-applying roll rotate relative to and in engagement with a portion of the strip of adhesive tape while it was being advanced to a cutting zone preparatory to a subsequent closure tape being cut therefrom. This also required that a rotating cutter or cutters move into slots in the tape-applying roll, resulting in residual adhesive material from the tape becoming lodged on the cutters and the tape-applying roll, which required frequent cleaning of the same so that the residual adhesive would not be picked up by the moving web. Also, to our knowledge, no means have been provided heretofore for automatically stopping rotation of the tape-applying roll and the feeding of the strip of tape from the supply source to the tape-applying roll, if for any reason, a closure strip was not being transferred from the supply strip of adhesive tape to the moving web each time a predetermined length of the moving web moved past the tape-applying roll.

Accordingly, it is an object of this invention to provide an efficient method and apparatus for forming and applying pressure sensitive fastener tabs to opposite longitudinal edges of a web, such as a web of diaper-forming material, moving at relatively high speed and which is particularly adapted for interposition in production-line manufacture.

It is another more specific object of this invention to provide an improved method and apparatus for forming and applying pressure sensitive fastener tabs to at least one longitudinal edge of a web, such as a web of diaper-forming material, moving in a predetermined path of travel in a substantially continuous manner through a tab forming and applying station, in which a strip of adhesive tape is moved through a cutting zone within the station and then cut transversely thereof each time a predetermined relatively short length of the strip passes through the cutting zone so as to form a respective fastener tab thereof, whereupon the strip is stopped and each successive tab is advanced away from the strip and into a position against the moving web each time a predetermined length of the web moves through the tab forming and applying station, and wherein the movement of the web through the station is stopped automatically in the event of failure of a fastener tab to be advanced away from the cutting zone and positioned against the web each time a predetermined length of the web moves past the tab forming and applying station.

Some of the objects and advantages of the invention having been stated, others will appear as the description proceeds when taken in connection with the accompanying drawings, in which FIG. 1 is a schematic plan view of equipment for carrying out the invention wherein the essential stations of the equipment are represented in the form of a block diagram with the tab forming and applying station of the present invention positioned between the web assembling and folding stations;

FIG. 2 is a perspective view of a partially prefolded disposable diaper as produced on the apparatus of FIG. 1 and particularly illustrating a pair of laterally opposed pressure sensitive fastener tabs with partially shielded adhesive faces and secured to opposite longitudinal edge portions of the diaper-forming web and adjacent one end of a corresponding individual diaper, FIG. 3 is a fragmentary elevation of the central portion of the diaper production line shown in FIG. 1 and illustrating the left-hand side of the tab forming and applying apparatus.

FIG. 7 is an enlarged fragmentary sectional view through one of the tab transferring or applying rolls taken substantially along line 7—7 in FIG. 5 and also illustrating some details of the cutting zone adjacent the tab applying roll;

FIG. 8 is a fragmentary view looking upwardly at the bottom of the cutting zone and the tab applying roll as viewed in FIG. 7;

FIG. 9 is a fragmentary vertical view through the cutting zone and the tab applying roll taken substantially along line 9—9 in FIG. 8;

FIG. 10 is an enlarged perspective view of the tab forming and applying apparatus as viewed looking at the right-hand side of FIG. 3, but showing some of the parts of the apparatus more in detail;

Figure 4:
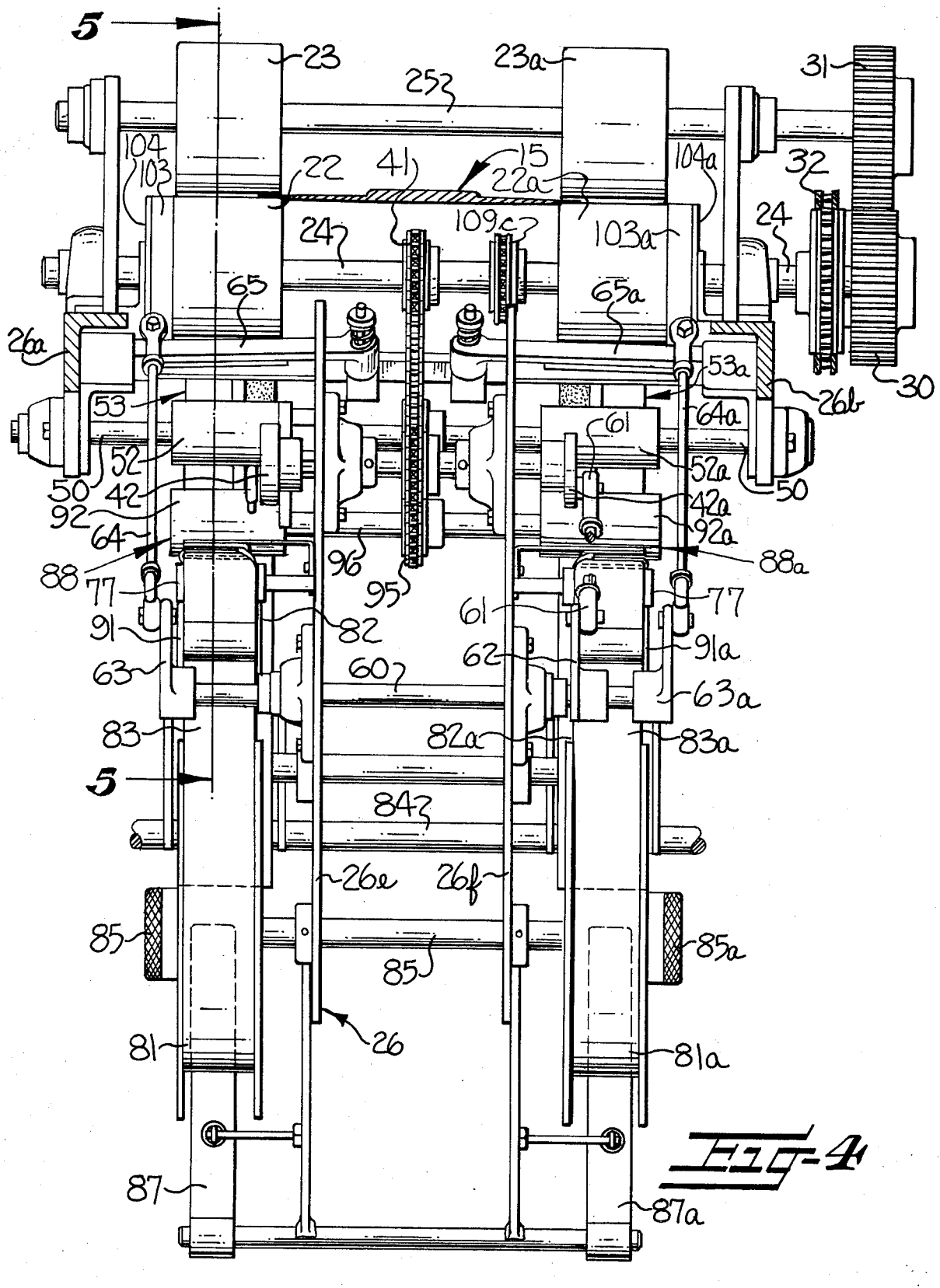
FIG. 4 is an enlarged fragmentary elevation of the tab forming and applying apparatus looking substantially along line 4—4 in FIG. 3.

Referring more specifically to the drawings, especially FIG. 1, as indicated earlier herein the fastener tab forming and applying method and apparatus of this invention are particularly devised for use in conjunction with machinery capable of production-line manufacture of disposable diapers. The machinery may be of the type disclosed and claimed in the aforementioned U.S. Pat. No. 3,661,680, now U.S. Pat. No. Re. 28,139, reissued Aug. 27, 1974, whose disclosure is incorporated herein by reference, and which also discloses a disposable diaper of the type with which this invention is concerned As shown in FIG. 1, a multi-layered diaper-forming web 15 is formed from several layers of sheet material in sheet assembling station or apparatus A driven by an electrically operable drive means or electric motor 16 which directs web 15, in substantially flat condition and at relatively high speed, through the tab forming and applying station or apparatus B of the present invention, and which will be later described. From the tab forming and applying station B, the diaper-forming web 15 passes through a folding station or apparatus C which folds the moving web longitudinally, separates previously partially slitted interconnected diaper sections of the web into individual diapers 15a (FIG. 2), and then transversely folds each successive diaper to complete the formation of the prefolded diapers 15a.

As disclosed in said patent, the web assembling station A forms the multi-layered diaper-forming web 15 of FIGS. 1, 2 and 3 by superimposing an elongate, fluid permeable, front cover sheet over a relatively narrow elongate moisture absorbent pad previously formed upon an elongate impervious backing sheet whose opposing longitudinal edges are adhesively secured to opposing longitudinal edges of the front cover sheet. As each successive predetermined length 15a of the web thus formed is advanced through the web assembling station A, it is embossed along a relatively narrow band transversely of the web 15 and substantially throughout the width thereof to interconnect the webs. Web 15 is scored or slitted at closely spaced lines substantially throughout its width along the center of each such embossed band.

The web 15 then is folded and separated into lengths in station C to form the individual diapers. A diaper 15a, thus formed, is illustrated in FIG. 2 wherein it will be observed that opposite ends of the prefolded diaper 15a are provided with narrow bands 15b of sparsely spaced indentations or embossed areas. It will also be observed that the opposing longitudinal edges of the diaper 15a, adjacent one of the embossed bands 15b at one end of the diaper, are provided with a pair of adhesive or pressure sensitive fastener tabs T, T' preferably secured to the aforementioned impervious sheet of which the diaper is formed, and each of which has a substantial length thereof projecting outwardly from the corresponding longitudinal edge of the diaper 15a.

Each fastener tab T, T' is formed of adhesive tape and the adhesive side of that portion of each tape T, T' projecting outwardly from the diaper 15a is provided with a mask or shield of release tape R which is creased and prefolded so that it may be readily pulled away from the adhesive face of the corresponding fastener tape when the diaper is to be secured about a baby's body. It is apparent that both the adhesive tape and the release tape R may be of the same width, but since the release tape is folded upon itself at the inner portion of each fastener tab T, T', the effective length of each release tab is less than the overall length of each respective tab T, T'.

The apparatus of the present invention for forming and applying a pair of the pressure sensitive fastener tabs T, T' to each successive predetermined length of the moving web 15 now will be described.

As best shown in FIG. 3, the diaper-forming web 15 is supported and guided in a predetermined substantially straight path through tab forming and applying station B on a pair of substantially horizontal plates 20, 21, the plate 21 being positioned forwardly of plate 20 or cut away to provide a small gap or gaps therebetween to accommodate a pair of axially aligned tab transferring or applying rolls 22, 22a. The proximal peripheral surface portions of rolls 22, 22a underlie and engage the lower surface of opposite longitudinal side edge portions of the moving web 15. Thus each roll 22, 22a and the tabs T, T' applied thereby are overlapped by the moving web 15. Since both tab applying rolls 22, 22a may be identical, except opposite hand, those parts associated with the tab applying roll 22a will bear the same reference characters as like or similar parts associated with the tab applying roll 22, with the letter a added, where applicable.

A pair of pressure rolls 23, 23a, disposed above the respective tab applying rolls 22, 22a, are adapted to press corresponding edge portions of web 15 against the upper peripheral surfaces of the respective tab applying rolls 22, 22a. Rolls 22, 22a, 23, 23a are driven to rotate at a peripheral speed corresponding to the rate of movement of web 15 in its course from the web assembling station A to the folding station C. Accordingly, it will be observed in FIGS. 4 and 10 that the pairs of rolls 22, 22a and 23, 23a are mounted on respective substantially horizontal shafts 24, 25 suitably journaled in the frame 26 of the apparatus and having respective intermeshing gears 30, 31 on corresponding ends thereof.

Figure 5:
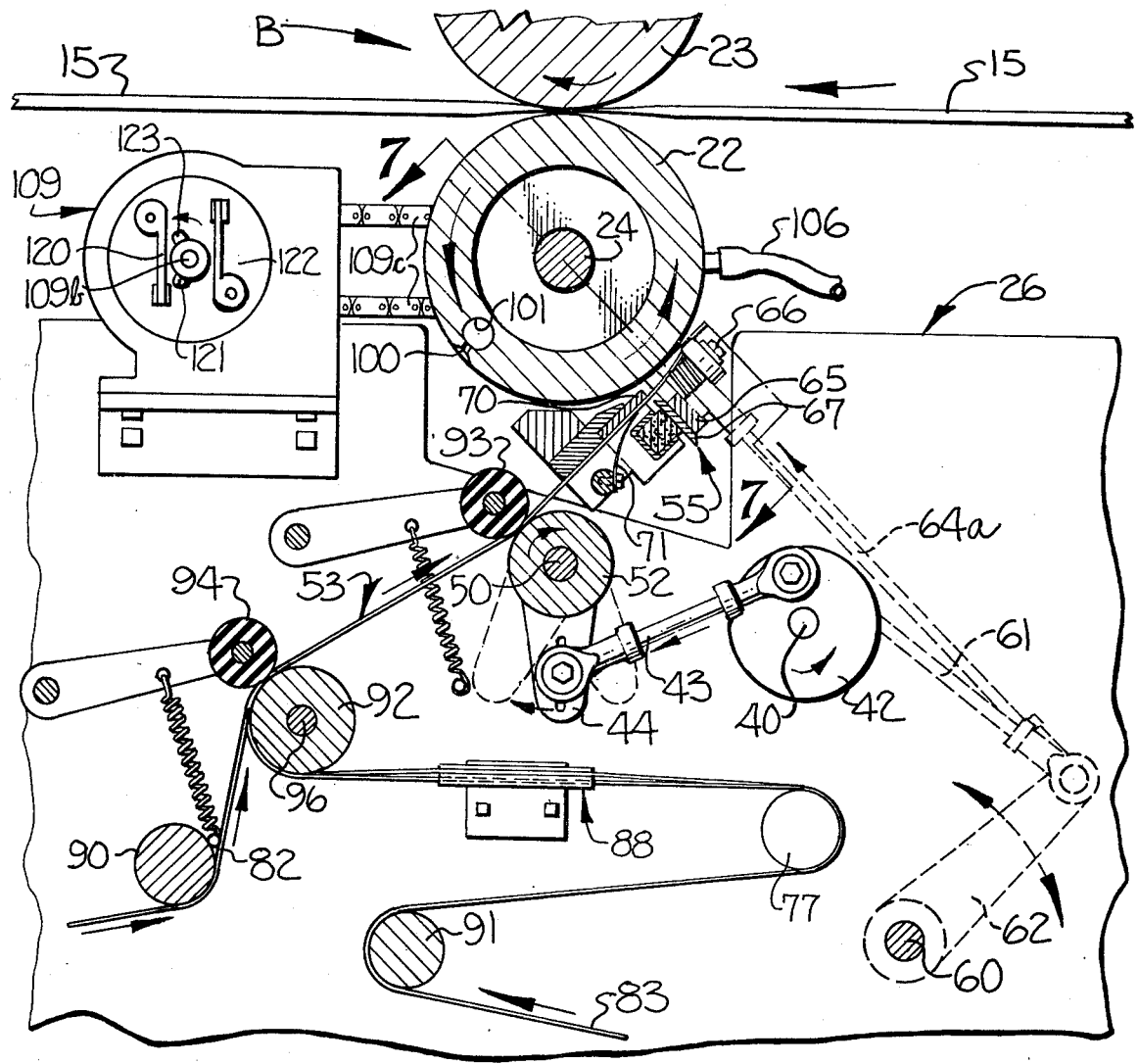
FIG. 5 is a further enlarged fragmentary vertical sectional view taken substantially along line 5—5 in FIG. 4.

As best shown in FIGS. 3, 4 and 5, essentially, frame 26 includes opposing side rails 26a, 26b with suitable cross rails 26c, 26d therebetween on which a pair of upright, laterally spaced frame plates 26e, 26f are suspended. Frame plates 26e, 26f are positioned relatively closer together than side rails 26a, 26b as shown in FIG. 4. Suitable sprocket and chain connections 32 connect shaft 24 to the main drive shaft 35 (FIG. 1) of the web assembling station A, which main drive shaft 35 is driven by electric motor 16 to deliver web 15 from web assembling station A at a substantially constant speed throughout normal operation thereof.

In addition to driving the tab applying rolls 22, 22a and pressure rolls 23, 23a, motor 16 (FIG. 1) also drives intermittently operable strip feeding means and normally inactive cutting means associated with each of the tab applying rolls 22, 22a. To this end, it will be observed in FIGS. 4 and 10 that shaft 24 is drivingly connected to a jack shaft 40 therebelow by suitable sprocket and chain connections 41. Shaft 40 is journaled on the spaced plates 26e, 26f of frame 26 and has suitable cranks 42, 42a thereon shown in the form of discs in FIG. 10.

Figure 6:
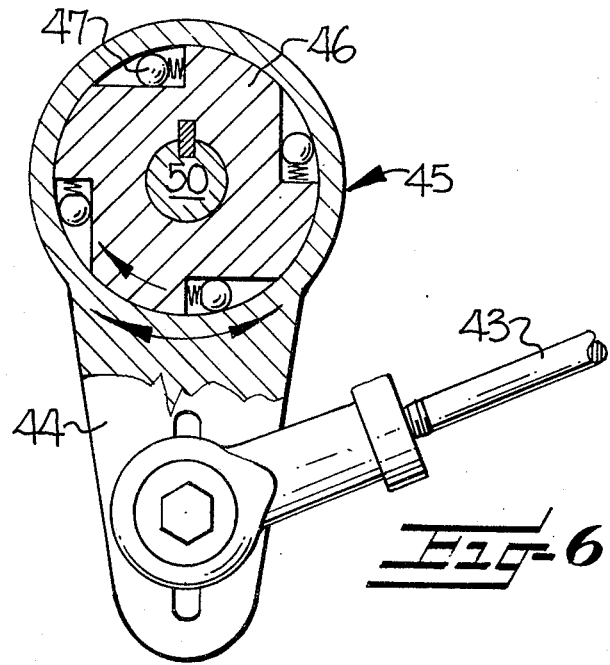
FIG. 6 is an enlarged fragmentary vertical sectional view, partially in elevation, showing a clutch mechanism associated with the adhesive strip feeding means shown in the central portion of FIG. 5.

A link 43 (FIG. 5, 6 and 10) connects crank 42 to a clutch arm 44 extending downwardly from and formed integral with the cylindrical housing of one-way stepping clutch 45. The housing of clutch 45 is loosely mounted on a hub 46 of well-known form having a plurality of balls 47 positioned in suitable offset cavities therein for engaging the inner peripheral surface of the housing of clutch 45. Clutch hub 46 is keyed on a shaft 50 having a pair of axially spaced primary strip feed rolls 52, 52a (FIG. 4 and 10) fixed thereon.

Feed rolls 52, 52a are arranged to feed respective composite strips 53, 53a (FIG. 4) of contiguous lengths of adhesive tape and release tape through respective cutting devices designated at 55, 55a and which define respective cutting zones closely adjacent the peripheries of the respective tab applying rolls 22, 22a, but remote from the path of travel of the web 15 thereover. In its course through cutting devices 55, 55a, each respective strip 53, 53a extends substantially tangentially of, but normally is spaced from the periphery of the respective tab applying roll, 22, 22a. However, as each strip 53, 53a is advanced a step and cut by the respective cutting device, it is so close to the respective roll 22, 22a as to be sucked against the periphery thereof. Since both cutting devices 55, 55a may be identical, except opposite hand, only the cutting device 55 will be described in detail and similar parts of the cutting device 55a will bear the same reference characters, where applicable, with the letter a added to avoid repetitive description.

It will be observed in the right-hand portion of FIG. 10 that the rotating crank or disc 42a imparts a rocking or reciprocating motion to a rocker shaft 60 through a link 61 and a crank arm 62. Cranks 63, 63a are fixed on opposite ends of rocker shaft 60 and may be considered parts of the respective cutting devices 55, 55a. Crank 63 has a link 64 extending therefrom to one end of a spring-loaded, reciprocatable cutter bar 65, pivoted as at 66, on the frame 26 and having a movable cutter blade 67 thereon. Cutter blade 67 cooperates with a stationary cutter blade or anvil also spaced from but disposed closely adjacent the periphery of tab applying roll 22.

The composite strip 53 is held against that surface of the stationary cutter blade 70 remote from the tab applying roll 22 by a suitable yieldable finger 71 (FIGS. 5 and 9). Since the blade carrying cutter bar 65 is pivoted at its inner portion as best shown in FIG. 10, it is apparent that blade 67 cooperates with the stationary blade 70 somewhat in the manner of scissors.

In order to prevent accummulations of lint, adhesive and other foreign matter on the cutter blade 67 and thereby to insure effective cutting of the composite strip 53 during each active stroke of the cutter blade 67, and to aid in preventing residual adhesive from soiling web 15, it will be observed in FIG. 7 that cutter blade 67 slides past and rubbingly engages an elongate, resilient, relatively narrow, sponge-like wiper element or wick 73 during each active and each inactive stroke of cutter blade 67. Wick 73 is saturated by a very lightweight or thin oil-like cleaning fluid which lubricates the blade 67 in addition to cleaning the same each time blade 67 moves relative to wiper element 73. Wiper element 73 is positioned in a suitable recess provided in a stationary bar 74 to which the discharge end of a conduit 75, leading from a suitable oil supply and pump 76, is suitably communicatively connected.

To facilitate the formation of each fastener tab so that it comprises a pressure sensitive adhesive tape portion secured to the corresponding diaper with a portion extending outwardly therefrom whose adhesive side is covered or shielded by a bent or partially folded tape R as in FIG. 2, each composite strip 53, 53a is formed by providing separate sources of supply of adhesive tape release tape adjacent and below each of the opposite longtiduinal side edge portions of the path of travel of web 15. To this end, it will be observed in FIGS. 3 and 4 that supply rolls 80, 81 of a pressure sensitive or adhesive tape 82 and a non-adhesive masking tape or release tape 83 are positioned in spaced relation from each other and mounted for substantially free rotation on respective shafts 84, 85 whose axes extend substantially parallel to each other and which are suitably supported in plates 26e, 26f of frame 26. It should be noted that the release tape 83 being drawn from supply roll 81 may be narrower than adhesive tape 82 and joined to tape 82 in offset relation thereto so as to expose about ¼ to ⅓ of the width of the adhesive tape, for example, for securement to web 15. However, it is preferred that both tapes 82, 83 are of about the same width so that about ¼ to ⅓ of the width of release tape 83 may be overfolded to provide pull tap portions on the fastener tabs to be formed from tapes 82, 83 while exposing a corresponding edge portion of adhesive tape 82. In either event, it can be appreciated that release tape 83 will have an effective width substantially less than that of the adhesive tape 82. Of course, the roll 81a (FIG. 4) and tapes 82a, 83a at the right-hand side of the machine correspond to elements 81, 82, 83 at the left-hand side of the machine.

Suitable braking fingers 86, 87 are suitably movably supported by frame 26 and engage the peripheral surface of the rolls 80, 81 of tapes 82, 83 so as to maintain the same under tension as they are advanced in engagement with respective idler rollers 90, 91. As preferred, release tape 83 then passes partially around a roll 77 and through a suitable tape bending or folding device 88 of well-known form which bends over or folds a narrow side portion 89 of tape 83 (FIGS. 8 and 10).

Tapes 82, 83 then converge inwardly toward each other into contiguous superimposed relation as they pass partially around a common driven secondary feed roll 92 from which the composite strip 53 thus formed of tapes 82, 83 passes to the corresponding primary feed roll 52 described heretofore. Feed rolls 52, 92 (FIG. 5) are engaged by respective springloaded pressure rolls 93, 94 to maintain the strip 53 in engagement therewith, and feed roll 52 is disposed closely adjacent and upstream of the respective cutting device 55.

Whenever a stepwise strip-feeding movement is imparted to feed roll 52 from drive shaft 24 via the elements 40–45 (FIGS. 4, 5, 6 and 10), a like stepwise movement is imparted to the upstream or secondary feed roll 92 through suitable sprocket and chain connections 95 (FIGS. 4 and 10) connecting shaft 50 is primary tape feed roll 52 to a shaft 96 on which the upstream feed roll 92 and its counterpart 92a are fixedly mounted. It is apparent by referring to FIGS. 4 and 5 that shafts 50, 60, 96 are suitably journaled in frame 26, and shafts 84, 85, along with the shafts on which idler rolls 77, 90, 91 are mounted, are all suitably supported in plates 26e, 26f of frame 26.

In order to transfer each successive fastener tab T and each successive fastener tab T' from the respective cutting zones 55, 55a (FIG. 10) away from the leading end of each respective adhesive strip 53, 53a each time a predetermined length 15a of web 15, equivalent to the desired length of a diaper 15a (FIG. 2), moves through fastener tab forming and applying station B, the circumference of each tab applying roll 22, 22a (FIG. 10) corresponds to each such predetermined length of web 15. Also, each tab applying roll has a peripheral speed corresponding to the speed of web 15, as effected by the sheet assembling station A, and each roll 22, 22a is provided with suction means for receiving each successive fastener tab as it is being cut from the corresponding adhesive strip and for holding the fastener tab in an operative position with its partially shielded adhesive side facing outwardly and until it has been applied to the corresponding longitudinal side edge portion of web 15.

Accordingly, it will be observed in FIGS. 7 and 9 that tab applying roll 22, which may be identical to roll 22a, is provided with a plurality of closely spaced tab-holding suction ports 100 arranged in a row extending substantially parallel to the axis of shaft 24. The suction ports 100 extend radially inwardly from the periphery of roll 22 and communicate with a common axial passage 101 whose outer end is in open communication with an arcuate groove or passage 102 formed in the proximal end of a stationary control means or suction header plate 103. Header plate 103 is frictionally and sealingly engaged by the adjacent outer end of the rotatable tab applying roll 22. A suitable compound bracket 104 attached to the outer end of suction header plate 103 serves to secure the same to the adjacent side rail 26a or 26b of frame 26 (FIG. 4) so that tab applying roll 22 rotates relative to header plate 103 during normal operation of the apparatus.

Suction lines 106 (FIG. 10) extend from a suitable source of suction, not shown, to the respective header plates 103, 103a for communication with the arcuate passages 102 so that, whenever the axial passage 101 in each roll 22, 22a is in registration with the corresponding arcuate passage 102, air flows into or suction is created in the corresponding row of tab holding suction ports 100. In this regard, it will be observed in FIG. 9 that the arcuate extent of the passage 102 is header plate 103 is such that a suction is created in ports 100, during each revolution of the corresponding tab applying roll 22, or 22a, before the row of suction ports 100 reaches the radial plane of the cutter blades 67, 70, and suction is maintained in suction ports 100 until corresponding fastener tab T being held against the periphery of the tab applying roll 22 by the ports 100 is transferred into engagement with and pressed against the lower surface of the corresponding outer edge portion of web 15. Thereupon, since arcuate passage 102 terminates at this point, the suction air flow is cut off as the ports 100 and the corresponding fasteners tab T or T' as the case may be, is released from the corresponding tab applying roll 22 or 22a. Of course, the pressure applying rolls 23, 23a also aid in pressing the successive fastener tabs T, T' against the lower surface of the moving web 15.

As heretofore indicated, the body release tape 83 is of substantially lesser width than adhesive tape 82 of which the composite adhesive strip 53 is formed, with the other longitudinal edges of the tapes 82, 83 being substantially aligned with each other so as to provide a substantial exposed adhesive side of the adhesive tape throughout the length of the composite strip 53 as shown in FIG. 8. This exposed portion is aligned beneath and thus overlapped by the corresponding outer edge portion of web 15 passing thereover, with the inner edge of the non-adhesive release tape portion 83 of the corresponding strip 53, and the fold lines of the release tape portions R of the tabs T formed therefrom, being substantially aligned with the adjacent outermost longitudinal side edge of web 15.

From the standpoint of economy and high production, it is desirable to operate the diaper-forming machinery at as high a rate as is practicable. Therefore, it is important that both a tab T and a tab T' are applied to each successive diaper 15a during machine production thereof so as to obviate the need for expending extra time and labor for inspecting and manually applying any missing fastener tabs to the prefolded diapers after they have been discharged from the diaper-forming machinery.

Accordingly, a pair of tab sensing means 106, 106a (FIGS. 3, 10, 11 and 12) is provided for sensing the absence of a fastener tab to be advanced away from either cutting zone 55 or 55a and applied to web 15 each time a predetermined length thereof moves past tab forming and applying station B. Each tab sensing means is effective to stop the longitudinal movement of web 15 whenever the absence of a fastener tab is sensed thereby. As preferred, the tab sensing means 106, 106a are in the form of respective photoelectric devices positioned downstream of the respective tab applying rolls 22, 22a and adjacent opposite sides of the path of travel of web 15.

The photoelectric devices 106, 106a are preferably of a well-known type having associated light emitting lamps therein, not shown, which normally direct respective beams of light a, a' across the paths of the respective successive fastener tabs T, T' projecting laterally from opposite side edges of web 15. Light beams a, a' normally are reflected back to the photoelectric devices 106, 106a by respective mirrors or reflectors 107, 107a aligned with the respective photoelectric devices 106, 106a. As shown in FIG. 10, photoelectric devices 106, 106a and reflectors 107, 107a are carried by respective brackets 108, 108a and are so positioned that successive tabs T, T' properly positioned in engagement with web 15 will pass between and momentarily interrupt the respective light beams a, a'.

The photoelectric devices 106, 106a are of a type which conduct electricity or are active in the absence of a light of predetermined intensity impinging thereon so that the photoelectric devices 106, 106a are rendered active upon interruption of the light beams a, a' by a corresponding pair of tabs T, T' and are effective, in a manner to be later described, to maintain energization of drive motor 16 (FIG. 1) so that the web 15 continues to move forwardly. However, a main timing mechanism 109 (FIG 5) is associated with a suitable electrical circuit (FIG. 12) and cooperates with photoelectric devices 106, 106a to interrupt energization of drive motor 16 and thus interrupt forward movement of web 15 upon the absence of a tab T or T', or upon the absence of both tabs T, T' interrupting the light beams a, a' at the desired instant to reflect that a pair of the tabs T, T' is properly positioned in engagement with web 15.

The photoelectric devices 106, 106a could be arranged to effect stoppage of the drive motor 16 independently of timing mechanism 109. However, it is preferred that the main timing mechanism 109 is included in the control system, because of the high speed of web 15, to insure that a sufficient time interval is provided, following detection of the absence of a fastener tab on web 15, so that the circuit will respond properly to the stop motor 16.

Figure 12:
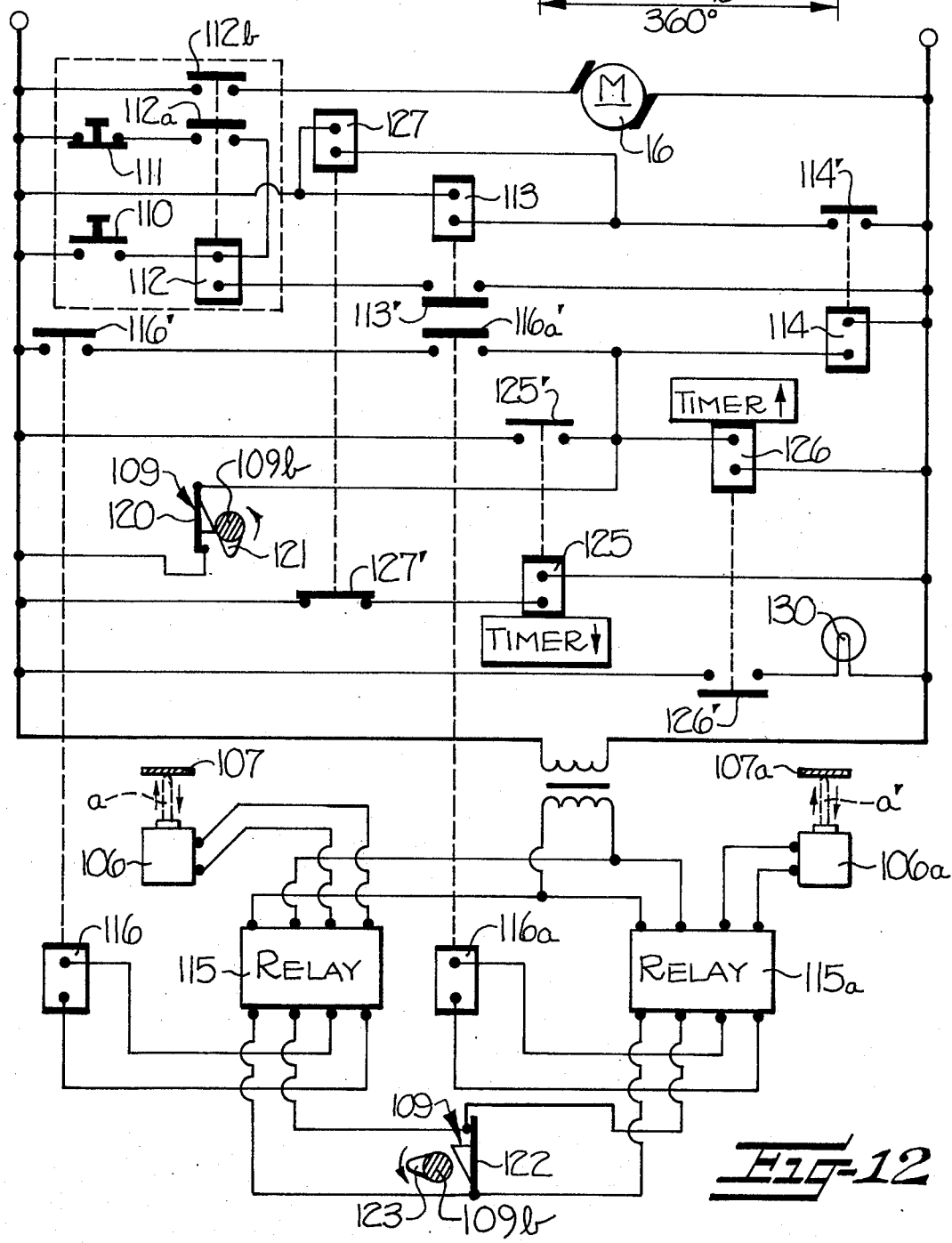
FIG. 12 is a schematic diagram of an electrical circuit for controlling the operation of the apparatus.

As shown in FIG. 12, the electrical circuit includes a normally open, manually operable, push-button start switch 110, a manually operable, normally closed, push-button stop switch 111, and an electromagnetic motor starter relay 112 provided with two normally open contacts sets 112a, 112b. A holding relay 113 includes a contact set 113' which is normally open but which, when closed, normally maintains energization of the motor starter relay 112 following a momentary closing of start switch 110. However, the normally open contact set 114' of a stop motion relay 114 is arranged in series with the coil of holding relay 113 and, since the contact set 113' of holding relay 113 is normally open, it follows that the coil of stop motion relay 114 also must be energized in order for motor 16 to be energized. Thus, the operation of the stop motion relay 114 and, consequently, the operation of electric motor 16, are controlled to some extent by the photoelectric devices 106, 106a, as will be presently described.

Accordingly, it will be observed in the lower portion of FIG. 12 that the photoelectric devices 106, 106a are electrically connected to respective normally open electronic latching relays 115, 115a. Latching relays 115, 115a are of a type well-known in the electrical industry which, upon being activated by the respective photoelectric devices 106, 106a being rendered momentarily conductive, will close a circuit until such time as the flow of current through the respective latching relay is interrupted. Thus, in this instance, each time that a pair of the properly positioned tabs T, T' interrupts the respective light beams a, a', and thereby causes the photoelectric devices 106, 106a to activate the respective latching relays 115, 115a, the latching relays 115, 115a, in turn, energize the coils of respective electromagnetic transitory relays 116, 116a. Contact sets 116', 116a' of the respective relays 116, 116a are in series with each other and also are in the series with the coil of stop motion relay 114.

At the instant that the transitory relays 116, 116a are activated and their contact sets 116', 116a' are closed by respective fastener tabs T, T' moving into the paths of the light beams a, a', a normally closed, first cam switch or timer switch 120 of main timer mechanism 109 occupies a closed position and already is completing a circuit through the coil of stop motion relay 114. However, thereafter and during the interval in which the transitory relays 116, 116a are still supposed to be active, a rotating cam 121 of timing mechanism 109 momentarily engages and opens the normally closed first timer switch 120.

After first timer switch 120 has returned to closed position, a normally closed second cam switch or timer switch 122 of the main timer mechanism 109 is engaged and momentarily opened by a rotating cam 123 which rotates in fixed relation with cam 121. It is apparent that cam 123 is out of phase relative to cam 121 and with respect to the positions of timer switches 120, 122. It should be noted that, upon second timer switch 122 being opened by cam 123, the circuit to both latching relays 115, 115a is interrupted so that they become inactive and thereby inactivate the transitory relays 116, 116a so that their respective contact sets 116', 116a ' return to their normally open positions.

It is thus seen that, upon failure of either or both of the transitory relays 116, 116a to be activated as a particular length of the web 15 moves past the photoelectric devices 106, 106a with either or both of a pair of the tabs T, T' missing from the corresponding length of web 15, the respective latching relay or relays 115, 115a will not be activated and, consequently, the respective transistory relays 116, and/or 116a will not be activated. Therefore, when the cam 121 subsequently engages and momentarily opens first timer switch 120, since the circuit cannot be carried through open contact sets 116', 116a' of the respective transitory relays 116, 116a to the coil of stop motion relay 114, it is apparent that first timer switch 120 will interrupt the circuit to the coil of stop motion relay 114, thus deenergizing the coils of relays 112, 113 and stopping operation of drive motor 16.

Referring again to the main timing mechanism 109, it is shown in FIG. 5 as being of a type generally as disclosed in U.S. Pat. No. 2,800,536 granted to Edward B. Farmer on July 23, 1957, the disclosure of which is incorporated herein by reference. As shown, timing mechanism 109 is suitably mounted on frame 26 and the cams 121, 123, are mounted at about 90° out of phase relative to each other on a shaft 109b driven by suitable sprocket and chain connections 109c with shaft 24. Switches 120, 122 are shown straddling cam shaft 109b.

Figure 11:
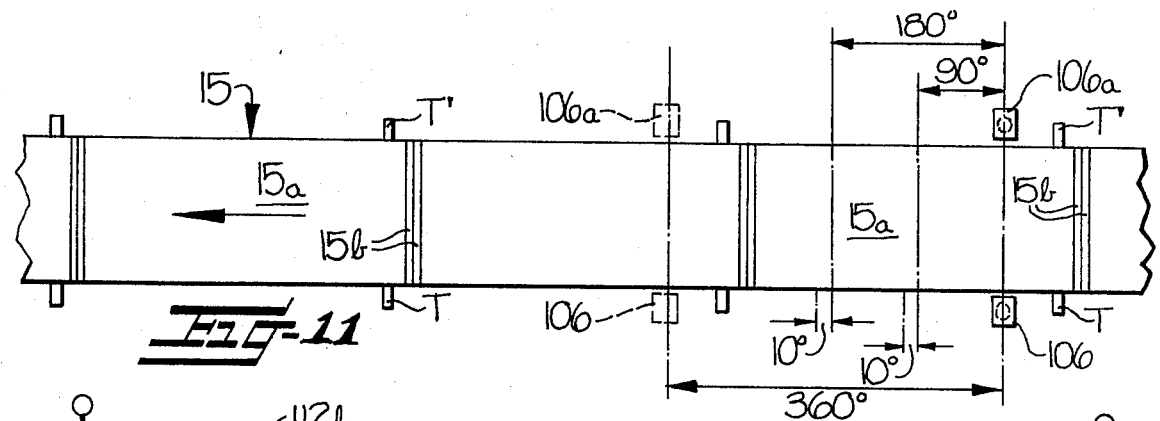
FIG. 11 is a schematic plan view of the web illustrating stages in the sequential detection of any absent fastener tabs and the stopping of the machine.

Shaft 109b rotates in unison with tab applying rolls 22, 22a and, the circumference of each roll 22, 22a corresponds to the length of each diaper 15a to be severed from web 15 (FIG 11), it follows that cams 121, 123 rotate one complete revolution during each cycle of the tab forming and applying station B. In other words, cams 121, 123 rotate one revolution or 360° during each movement of a length of the web equivalent to a diaper 15a past the photoelectric sensing devices 106, 106a, as indicated in FIG. 11.

It is desirable to provide a visual or audible warning signal, adjacent the tab forming and applying station B, which will be activated each time the absence of a tab T and/or T' on web 15 causes stoppage of motor 16. Further, it is desirable to reset the circuit by automatically energizing the coil of stop motion relay 114 immediately following the deenergizing of motor 16 effected by the opening of contact set 114' of stop motion relay 114. Otherwise, the subsequent manual closing of start switch 110 would not effect operation of motor 16, as would be necessary in order to correct the malfunction of the machine or to resume normal operation of the machine.

Accordingly, it will be observed in FIG. 12 that the circuit also comprises electromagnetically operable timer relays or time-delay-relays 125, 126 and a timer-triggering relay 127. Timer relays 125, 126 are provided with respective normally open contact sets 125', 126' which are closed immediately upon energization of the coils of the respective timer relays and which then remain closed for respective pre-established intervals regardless of whether energization of the latter coils is continued or stopped immediately. The contact set 127' of triggering relay 127 is normally closed, but is held open during normal operation of the machine.

The coil of triggering relay 127 is arranged in parallel with the coil of holding relay 113 and thus is energized and deenergized by the respective closing and opening of the contact set 114° of stop motion relay 114. When the coil of relay 127 is deenergized, the consequent closing of its normally closed contact set 127' energizes the coil of timer relay 125. As heretofore indicated, immediately upon initial energization of the coil of timer relay 125, contact set 125' closes and will then return to open position after a delay of a relatively short time interval of; e.g., five seconds, even though the coil of timer 125 may remain energized.

Whenever the contact set 125' is moved to the closed position, it momentarily completes a circuit to the timer 126 so that the coil thereof immediately closes the normally open contact sets 126' to energize a normally inactive, electrically operable warning device 130 shown in the form of a lamp in FIG. 12. Thus, lamp 130 will remain closed for a predetermined period of time thereafter such as to insure that an operator may be alerted by the warning device 130 to take any corrective measures which may be required.

The method of operation of the apparatus may be generally understood from the foregoing description. However, a summary of the operation will now be given.

From the foregoing description it is quite clear that main drive motor 16 (FIGS. 1 and 12) is energized by the momentary manual closing of start switch 110 (FIG. 12), which effects energization of the coil of relay 112 through the then closed contact sets 113', 114' of relays 113, 114. The contact sets 112a, 112b of starter relay 112 then move to closed position and the flow of current through the coil of starter relay 112 is maintained through the stop switch 111 and contact set 112a as contact set 112b establishes the circuit to drive motor 16.

It is apparent that the composite strips 53, 53a (FIG. 4) are being formed continuously during operation of the tab forming and applying station B. It is also apparent that the strips 53, 53a are repeatedly being severed at predetermined intervals to form the relatively narrow fastener strips T, T' therefrom which are, in turn, applied against the lower surfaces of web 15 adjacent the opposite side edges thereof as each diaper-size length of web 15 moves past the tab applying rolls 22, 22a. Since the shield or release tapes 83, 83a are folded longitudinally before they contact adhesive tapes 82, 82a it can be appreciated that the tab release strips R (FIG. 2) each have short overfolded end portions 89 adjacent the exposed adhesive portion of the respective fastener tab T, T', so the user may readily grasp and pull such overfolded end portions of the release strips R and expose the adhesive faces of the tabs T, T' when fastening a diaper 15a about a baby's body.

As heretofore indicated, assuming that all of the production-line stations A, B, C of FIG. 1 are in proper operating condition with the pair of fastener tabs T, T' last applied to the web 15 occupying a position upstream of photoelectric devices 106, 106a substantially shown in FIG. 11, it then may be assumed that first timer switch 120 (FIGS. 4 and 12) is closed, thus assuring energization of the coil of stop motion relay 114. The contact set 114' then occupies closed position, thus energizing the coils of relays 113, 127 and causing contact sets 113' be held closed while contact set 127' is held open. The circuit to the coils of the remaining relays 112, 115, 115a, 116, 116a, 125 and 126 then would be open. Thus, upon the manual momentary closing of start switch 110, motor starter relay 112 is closed to energize motor 16 and start the machine in the manner heretofore described.

Since both of the tabs T, T' in the right-hand portion of FIG. 11 have been properly applied to web 15, as the latter fastener tabs pass over the photoelectric devices 106, 106a, both contact sets 116', 116a' are closed in the manner heretofore described. Thereafter; e.g., about 90° in a cycle in the operation of the rotary timing mechanism 109, cam 121 momentarily opens the first time switch 120 for an interval of about 10° of a cycle, as indicated in FIG. 11.

Although switch 120 is opened, since contact sets 116', 116a' are both in a closed state, normal operation of the tab forming and applying station B remains uninterrupted. Subsequently, after first timer switch 120 closes and at about 180' in a cycle of timing mechanism 109, cam 123 opens switch 122 (FIG. 12) to interrupt the circuit to the coils of transitory relays 116, 116a so that the contact sets 116', 116a' thereof return to open position, such normal cycle in the operation of the tab forming and applying station B being repeated as each successive properly positioned pair of tabs T, T' approaches the photoelectric devices 106, 106a.

In the absence of a fastener tab being properly positioned and projecting laterally from either or both side edges of web 15 as the corresponding portion of web 15 approaches photoelectric devices 106, 106a, the operation of the electrical circuit is as follows:

1. In the event that a predetermined portion of the web 15 to which fastener tabs should have been applied does not have one or the other of the tabs T, T' applied thereto before the corresponding portion of the web 15 moves past the photoelectric devices 106, 106a, the respective photoelectric device or devices will fail to activate the corresponding latching relay 115 and/or 115a so that the respective transistory relay 116 and/or 116a will remain inactive and the respective contact sets 116', 116a' will remain in open position. Thus, when the latter portion of web 15 reaches the 90' position in a cycle thereof, the opening of the switch 120 by cam 121 will interrupt the circuit to the coil of relay 114, thus stopping the flow of electrical energy to motor 16 and stopping further operation of the production-line stations A, B, C of FIG. 1.

2. Inactivation of the coil of stop motion relay 114 also breaks the circuit to the coil of relay 127 so that its contact sets 127' return to their normally closed position.

3. Return of contact set 127' to its normally closed position energizes the coil of timer relay 125 to immediately close the normally open contact set 125' thereof. Thus, even though switch 120 and one or the other or both contact sets 116', 116a' then occupy open position, the closing of timer contact set 125' initiates a cycle in the operation of timer relay 126 for illuminating the lamp 130 while also restoring the flow of electrical energy through the coil of stop motion relay 114.

4. Restoration of electrical energy to the coil of relay 114 closes contact set 114' closes to effect energization of the coils of relays 113, 127, thereby closing contact set 113' and opening contact set 127'. However, the circuit to drive motor 16 remains open.

5. Each time the coil of timer relay 125 is energized initially, its contact set 125' closes immediately and remains closed for a relatively short dwell period of, say, five seconds, whereupon the contact set 125' returns to the open state regardless of whether or not the coil of timer relay 125 remains energized.

6. Since the flow of electrical energy through the coil of stop motion relay 114 was restored and effected closing of the contact set 113', the electric motor 16 may again be started manually.

7. Normally, by the time that the dwell period, during which the timer relay contact set 125' occupies closed position, has expired, the operator will have closed the manual start switch 110 to restart the machine or at least to jog the machine so that switch 120 may close. Otherwise, upon the end of the dwell period of contact set 125', it will open and inactivate the coil of stop motion relay 114. Thus, the steps 2–6 described above will be repeated.

It is thus seen that, as long as a pair of fastener tabs T, T' is properly positioned and projecting from opposite sides of the web as each successive diaper 15a thereof passes through the lateral plane of the photoelectric devices 106, 106a, the apparatus may continue to operate in a normal manner. Conversely, whenever a fastener T, T' is not present at the desired location adjacent each diaper 15a in web 15, it is apparent that the respective photoelectric device will then sense the absence of such fastener tab so that first timer switch 120 subsequently will interrupt the flow of electrical energy through the coil of stop motion relay 114 and thus interrupt the operation of electric motor 16.

In the drawings and specification there has been set forth a preferred embodiment of the invention, and although specific terms are employed, they are used in a generic and descriptive sense only and not for the purposes of limitation.

What is claimed is:

1. In an apparatus for the manufacture of disposable diapers or other articles having spaced apart fastener tabs, labels or strips at predetermined locations thereon and including means for continuously moving material being manufactured into such articles through said apparatus, and means for applying such fastener tabs, labels or strips at the predetermined locations to the moving material; the combination therewith of:

electrically operated drive means operatively connected with said material moving means and said tab, label or strip applying means for driving both of said means;

sensing means positioned adjacent said tab, label or strip applying means and downstream of the path of travel of the material therefrom for sensing the passage of the tabs, labels or strips applied on the moving material; and electric circuit means connected with said sensing means and with said drive means for normally operating said drive means and being responsive to said sensing means for stopping operation of said drive means when said sensing means fails to sense the passage of a tab, label or strip at a predetermined location on the moving material as it passes said sensing means, whereby operation of said material moving means and said tab, label or strip applying means is stopped in the event of the failure of a tab, label or strip having been applied to the moving material at a predetermined location for repair of said apparatus.

2. In an apparatus, as set forth in claim 1, in which said sensing means comprises photoelectric cell means.

3. In an apparatus, as set forth in claim 2, in which said electric circuit means includes an electric circuit connected between a source of electrical energy and said electrically operated drive means for effecting the flow of electrical energy therebetween for the operation of said drive means, a normally closed switch contact set in said circuit for maintaining the flow of electrical energy therethrough during normal operation, timer means in said circuit connected with said normally closed switch contact set for momentarily opening said normally closed switch contact set during predetermined timed periods, and a normally open switch contact set in said circuit connected in parallel with said normally closed switch contact set and being connected with and responsive to said photoelectric cell sensing means for being closed thereby for the predetermined timed periods during which said normally closed switch contact set is opened by said timer means upon said photoelectric cell sensing means sensing the passage of a fastener tab, label or strip on the moving material for maintaining the flow of electric energy through said circuit, whereby, upon the absence of a fastener tab, label or strip moving past said photoelectric cell sensing means, said normally open switch contact set will not be closed before said timer means momentarily opens said normally closed switch contact set and the opening of the normally closed switch contact set will interrupt the flow of electrical energy through said circuit which will interrupt operation of said electrically operated drive means for stopping operation of said material moving means and said means for applying the fastener tabs, labels or strips.

4. In an apparatus, as set forth in claim 3, in which said timer means comprises a rotating cam having a predetermined profile and a cam follower in contact with said cam and operatively connected with said normally closed switch contact set for momentarily opening said normally closed switch contact set during predetermined timed intervals of the rotation of said cam and during which time the predetermined location on the moving material at which the fastener tab, label or strip is intended to be applied passes under said photoelectric cell sensing means.

5. In a driven apparatus for the manufacture of successively formed disposable diapers and including means for applying adhesive fastener tabs at predetermined locations to the successive diapers as they travel through said apparatus in an elongate path of travel for manufacture; the combination therewith of:

electrically operated drive means operatively connected with said diaper manufacturing apparatus and said adhesive tab applying means for driving same;

sensing means positioned adjacent said adhesive tab applying means and downstream of the path of travel of the successive diapers therefrom for sensing the passage of the adhesive tabs applied onto the diapers; and electric circuit means connected with said sensing means and with said drive means for normally operating said drive means and being responsive to said sensing means for stopping operation of said drive means when said sensing means fails to sense the passage of an adhesive tab at a predetermined location on the moving diapers as they pass said sensing means, whereby operation of said diaper manufacturing apparatus and said adhesive tab applying means is stopped for repair in the event of the failure of an adhesive tab having been applied to the moving diapers at a predetermined location.

6. In an apparatus, as set forth in claim 5, in which said sensing means comprises photoelectric cell means and in which said electric circuit means includes an electric circuit connected between a source of electrical energy and said electrically operated drive means for effecting the flow of electrical energy therebetween for the operation of said drive means, a normally closed switch contact set in said circuit for maintaining the flow of electrical energy therethrough during normal operation, timer means in said circuit connected with said normally closed switch contact set for momentarily opening said normally closed switch contact set during predetermined timed periods, and a normally open switch contact set in said circuit connected in parallel with said normally closed switch contact set and being connected with and responsive to said photoelectric cell sensing means for being closed thereby for the predetermined timed periods during which said normally closed switch contact set is opened by said timer means upon said photoelectric cell sensing means sensing the passage of a fastener tab on the moving diapers for maintaining the flow of electric energy through said circuit, whereby, upon the absence of a fastener tab moving past said photoelectric cell sensing means, said normally open switch contact set will not be closed before said timer means momentarily opens said normally closed switch contact set and the opening of the normally closed switch contact set will interrupt the flow of electrical energy through said circuit which will interrupt operation of said electrically operated drive means for stopping operation of said diaper manufacturing apparatus and said means for applying the adhesive fastener tabs.

7. In an apparatus, as set forth in claim 5, in which said adhesive fastener tab applying means applies fastener tabs at predetermined locations on each longitudinal edge of the successive diapers as they travel through said apparatus, and in which said sensing means comprises a pair of photoelectric cell devices positioned adjacent the path of travel of each longitudinal edge of the successive diapers as they travel downstream from said adhesive tab applying means through said apparatus.

* * * * *